US010090857B2

(12) United States Patent
Bhola et al.

(10) Patent No.: US 10,090,857 B2
(45) Date of Patent: Oct. 2, 2018

(54) METHOD AND APPARATUS FOR COMPRESSING GENETIC DATA

(75) Inventors: Vishal Bhola, New Dheli (IN); Shyamsunder Ajit Bopardikar, Bangalore (IN); Rangavittal Narayanan, Bangalore (IN); Kyu-Sang Lee, Ulsan (KR); Tae-Jin Ahn, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 846 days.

(21) Appl. No.: 13/492,505

(22) Filed: Jun. 8, 2012

(65) Prior Publication Data

US 2013/0031092 A1     Jan. 31, 2013

(30) Foreign Application Priority Data

Apr. 26, 2010   (IN) ...................... 1982/CHE/2011CS
Jun. 10, 2011   (IN) ...................... 1982/CHE/2011PS
May 25, 2012   (KR) ...................... 10-2012-0056228

(51) Int. Cl.
     *G06F 19/00*      (2011.01)
     *H03M 7/46*      (2006.01)
     *H03M 7/40*      (2006.01)

(52) U.S. Cl.
     CPC ............. *H03M 7/46* (2013.01); *H03M 7/40* (2013.01)

(58) Field of Classification Search
     CPC ............. G06F 12/0207; G06F 12/04; G06F 17/30153; G06F 17/30463; G06F 17/30315; G06F 17/30796; G06F 21/64
See application file for complete search history.

(56) References Cited

U.S. PATENT DOCUMENTS

| | | | | |
|---|---|---|---|---|
| 6,894,628 B2* | 5/2005 | Marpe et al. | ................. | 341/107 |
| 8,847,799 B1* | 9/2014 | Kennedy et al. | ............... | 341/87 |
| 2013/0166518 A1* | 6/2013 | Mande et al. | ................ | 707/693 |

FOREIGN PATENT DOCUMENTS

| | | |
|---|---|---|
| JP | 2005-286371 A | 10/2005 |
| JP | 2006-262462 A | 9/2006 |
| KR | 1020040070438 A | 8/2004 |
| KR | 1020110025359 A | 3/2011 |

OTHER PUBLICATIONS

Witten et al. Arithmetic coding for data compression, Communication of the ACM Jun. 1987 vol. 30 No. 6 p. 520.*
Chen et al. DNACompress: fast and effective DNA Sequence compression, Bioinformatics, vol. 18, No. 12, 2002 o 1696-1698.*

(Continued)

*Primary Examiner* — Mary K Zeman
(74) *Attorney, Agent, or Firm* — Leydig, Voit & Mayer, Ltd.

(57) ABSTRACT

A method of compressing sequence data in a text-based format, the method involving parsing text of the sequence data into a plurality of fields, identifying encoding algorithms that achieve greatest compression gains with respect to the plurality of fields based on collected statistics, and generating a bitstream, compressed from the sequence data, by encoding the sequence data using the identified encoding algorithms.

26 Claims, 7 Drawing Sheets

Specification includes a Sequence Listing.

(56) References Cited

OTHER PUBLICATIONS

Duc Cao et al. A simple statistical algorithm for Biological Sequence Compression, IEEE Data Compression conference (DDC'07) 2007.*
Ansorge, Wilhelm J., "Next-Generation DNA Sequencing Techniques," *New Biotechnology*, Apr. 2009, 196-203, 25-4.
Cock et al., "The Sanger FASTQ File Format for Sequences with Quality Scores, and the Solexa/Illumina FASTQ Variants," *Nucleic Acids Research*, 2010, 1727-1771, 38-6.
Deorowicz et al., "Compression of Genomic Sequences in FASTQ Format," *Bioinformatics Advance Access*, Jan. 19, 2011, 1-3, Oxford University Press.
Shendure et al., "Next-Generation DNA Sequencing," *Nature Biotechnology*, Oct. 2008, 1135-1145, 26-10.
Mardis, Elaine R., "Next-Generation DNA Sequencing Methods," *Annu. Rev. Genomics Hum. Genet.*, 2008, 387-402, 9.
Tembe et al., "G-SQZ: Compact Encoding of Genomic Sequence and Quality Data," *Bioinformatics*, 2010, 2192-2194, 26-17.

* cited by examiner

| Read # 1 | @title line and optional description<br>Sequence<br>+optional repeat of line 1<br>Quality values |
| --- | --- |
| . . . | . . . |
| Read # N | @title line and optional description<br>Sequence<br>+optional repeat of line 1<br>Quality values |
|  | EOF |

METHOD AND APPARATUS FOR COMPRESSING GENETIC DATA

CROSS-REFERENCE TO RELATED APPLICATIONS

The present application claims priority to Indian Patent Application No. 1982/CHE/2011(PS) filed Jun. 10, 2011, Indian Patent Application No. 1982/CHE/2011(CS) filed Apr. 26, 2012, and Korean Patent Application No. 10-2012-0056228 filed May 25, 2012.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 905 Byte ASCII (Text) file named "710546_ST25.TXT," created Oct. 9, 2012.

BACKGROUND

1. Field

The present disclosure relates to bio-informatics, and more particularly, to a method and apparatus for compressing next generation sequencing (NGS) data in an FASTQ file format.

2. Description of the Related Art

With the continuous development of DNA (deoxyribonucleic acid) sequencing techniques, an enormous amount of DNA read sequences are being generated. Next generation sequencing (NGS) instruments generate huge amounts of genomic data along with multiple annotations such as quality scores and other meta-information such as read identifiers, instrument names, flow cell lanes and the like. The number of reads in NGS files may range from hundreds of millions to billions, depending on the species sequenced and the coverage as known from the current state of the art, leading to file sizes of the order of MBs (megabytes) to GBs (gigabytes). The constantly increasing throughput poses challenges in terms of storage and management of the sequencing data and this necessitates the use of an efficient compression utility so as to compactly encode the data.

With the advent of high throughput sequencing technologies, there is a remarkable increase in the volumes of genomic data. The cost overhead involved in the storage and management of the huge volumes of sequencing data generated by the next generation sequencing instruments are also increased. The storage, management and transfer of such huge data mandate the use of an efficient compression utility so as to minimize the involved cost overheads. The files output by these instruments range from MBs to GBs in size. Furthermore, these files also contain multiple annotations in addition to the DNA sequence and general purpose text compression utilities like bzip and gzip that do not perform well with respect to these file formats.

FASTQ format is a text-based format for storing both a biological sequence (usually, a nucleotide sequence) and its corresponding quality scores. Typically, NGS data is stored in the FASTQ file format and has become a de facto standard for storage of sequenced read data. This information is used by scientists in various applications such as de novo sequencing, assembly applications as well as re-sequencing applications. Hence, the compression technique to be used should be lossless or near-lossless so as to preserve all the essential information.

Although a large number of methods exist for DNA sequence compression, the data involved is not annotated as in the NGS data formats. Some compression methods employ reference sequences so as to encode only differences within the reads with respect to the reference. However, a reference sequence may not be readily available in many cases especially when sequencing a new species or organism. Also, because all reads do not align with the reference genome, large chunks of data that still need to be encoded are left behind.

From the above-mentioned reasons, it is evident that existing methods do not address the problem of cost overhead involved in the storage and management of the huge volumes of sequencing data generated by the NGS instruments. Also, the current methods do not employ efficient mechanisms by which the next generation sequencing data in FASTQ file format may be compressed by suitable encoding techniques.

SUMMARY

Provided are methods and apparatuses for compressing genetic data such as next generation sequencing (NGS) data.

Additional aspects will be set forth in part in the description which follows and, in part, will be apparent from the description, or may be learned by practice of the presented embodiments.

According to an aspect of the present disclosure, a method of compressing sequence data in a text-based format includes operations of parsing a text of the sequence data into a plurality of fields according to information included in the text; collecting statistics with respect to a symbol included in each of the plurality of fields; for each of the plurality of fields, identifying an encoding algorithm that achieves greatest compression gains with respect to the field based on the collected statistics; and generating a bitstream, compressed from the sequence data, by encoding the sequence data using the identified encoding algorithms.

According to another aspect of the present disclosure, a computer-readable recording medium has recorded thereon a program for executing a method of compressing sequence data.

According to an aspect of the present disclosure, an apparatus for compressing sequence data in a text-based format includes a parsing unit for parsing a text of the sequence data into a plurality of fields, according to information included in the text; a statistics collecting unit for collecting statistics with respect to a symbol included in each of the plurality of fields; an encoding algorithm identifying unit for identifying, for each of the plurality of fields, an encoding algorithm that achieves greatest compression gains with respect to the field based on the collected statistics; and a compressing unit for generating a bitstream, compressed from the sequence data, by encoding the sequence data using the identified encoding algorithms.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figures 1, 2A:
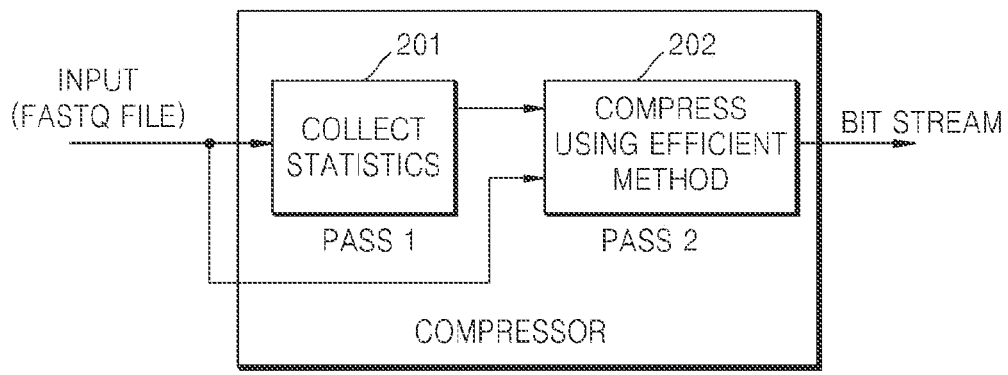
FIG. 1 illustrates a typical FASTQ file format for storing next generation sequencing (NGS) data, according to an embodiment of the present invention.
FIG. 2A illustrates a function of a compressor with an input FASTQ file, according to an embodiment of the present invention.

Reference will now be made in detail to embodiments, examples of which are illustrated in the accompanying drawings. However, the examples used herein are intended merely to facilitate an understanding of ways in which the embodiments herein can be practiced and to further enable those of ordinary skill in the art to practice the embodiments herein. Accordingly, the examples should not be construed as limiting the scope of the embodiments herein. Descriptions of well-known components and processing techniques are omitted so as to not unnecessarily obscure the embodiments herein. However, it will be obvious to those of ordinary skill in the art that the embodiments may further include general components in addition to the components.

Expressions such as "at least one of," when preceding a list of elements, modify the entire list of elements and do not modify the individual elements of the list.

The embodiments herein achieve a method and system to efficiently compress next generation sequencing (NGS) data or genomic data in a FASTQ file format. However, the method may be applied to any suitable text-based formats that are employed in DNA sequence compression methods. The method identifies various fields in a FASTQ file such as title information, sequence data and quality data, and then separates these fields. The method independently processes each of all of these fields in a two-pass manner. In the first pass, the statistics (e.g., length, type (alphanumeric/numeric), delimiter, etc.) are observed so as to determine the efficient encoding method for each sub-section of the fields. The respective fields are encoded in the second pass.

Hereinafter, with reference to FIGS. 1 through 6, similar reference numerals denote corresponding features that are consistent throughout the figures.

FIG. 1 illustrates a typical FASTQ file format for storing next generation sequence data, according to an embodiment of the present invention. Referring to FIG. 1, a single FASTQ file consists of text and quality information related to a plurality of reads. The FASTQ file format consists of 4 lines per sequence read—Title, DNA Sequence, Plus and Quality information. However, there may be no formal standardization of the format. Format description and variants of FASTQ format are known from the current state of the art. Moreover, the number of fields in the title line is not limited and may include any length of optional description following a sequence identifier.

FIG. 2A illustrates the function of the compressor with the input FASTQ file, according to an embodiment of the present invention. In the first pass (pass 1) where statistics of the component of the FASTQ file are collected (operation 201), the input FASTQ file is input to the compressor, and in the second pass (pass 2), the FASTQ file is compressed by using the most efficient method/mechanism from among the identified mechanisms (operation 202). Finally, the compressed bit stream is sent to the decompressor to retrieve the original FASTQ file.

Figure 2B:
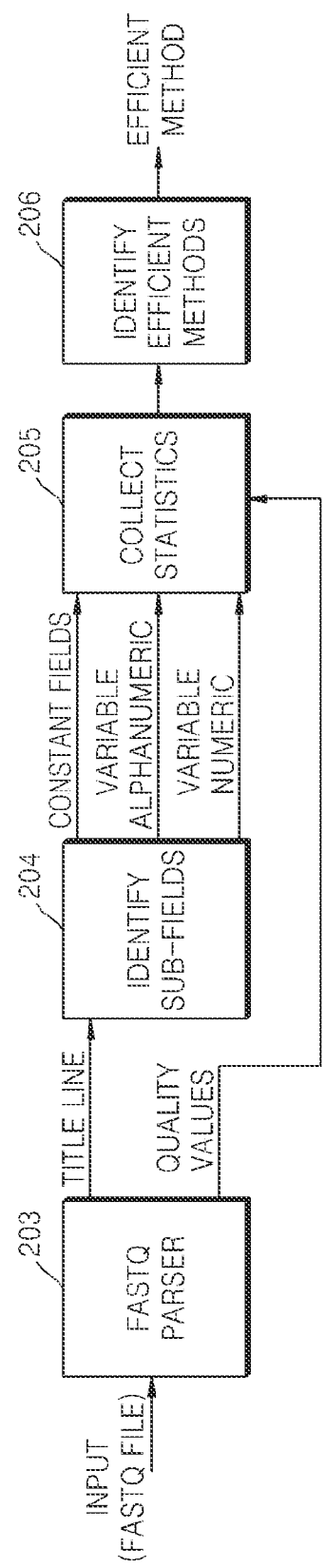
FIG. 2B illustrates a first pass performed to compute statistics and to identify efficient methods for each sub-field corresponding to text information and various representations of quality scores, according to an embodiment of the present invention.

FIG. 2B illustrates the first pass performed to compute the statistics and to identify the efficient methods for each sub-field corresponding to text information and various representations of quality scores, according to an embodiment of the present invention. Referring to FIG. 2B, a FASTQ file is input to a FASTQ parser 203. The FASTQ file is split into its components such as title line, and quality values. Then, in operation 204, the method identifies the different fields in the title line. In the present embodiment, the title line may be split into constant fields, variable alpha-numeric fields and variable numeric fields and so on. Furthermore, in operation 205, the method collects statistics for the title line fields and for quality values. In operation 206, further efficient methods to encode the text fields and quality values among the plurality of mechanisms are identified, for instance, by estimating entropies. Finally, the most efficient method is adopted in the second pass for efficient encoding.

In an embodiment, the method detects inconsistencies in title information organization in a file, based on periodic checking of the title lines in the file, and then efficiently represents the title lines in the event of these inconsistencies.

In the present embodiment, the method identifies the origin (such as SoLiD, illumine, 454, Helicos and the like) of the high throughput (NGS) sequencing data so as to perform parsing based on the title line information used to rapidly identify the various fields, which may be used to compress the data efficiently.

In the present embodiment, in a partial process of the first pass, the statistics for each of the fields corresponding to text and quality information until the point of convergence is computed. This information is used to determine the efficient encoding method for respective fields in the FASTQ file.

Figure 2C:
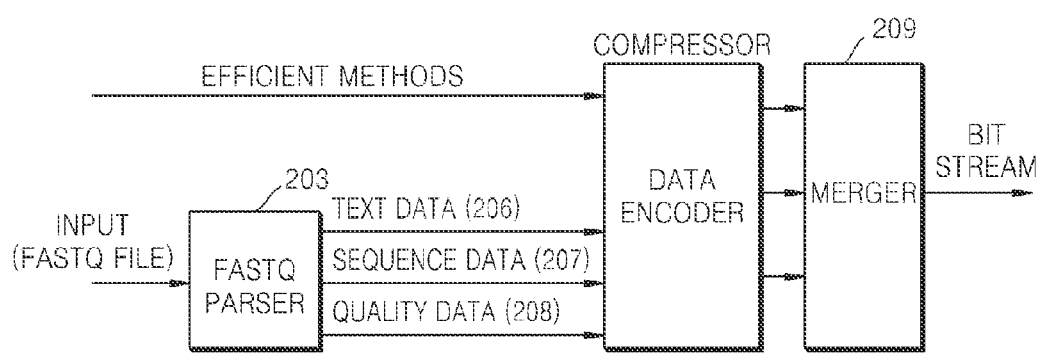
FIG. 2C illustrates a second pass performed using the efficient methods, according to an embodiment of the present invention.

FIG. 2C illustrates the second pass including compression performed using the efficient methods, according to an embodiment of the present invention. A FASTQ file is input, and the FASTQ parser 203 splits the file into text fields, DNA sequence and quality values. Then, the respective encoders for text data 206, sequence data 207, and quality data 208 encode the information based on the efficient methods identified in the first pass. The encoded bit-streams are fed into the merger 209 which outputs the unified compressed bit stream.

Figure 2D:
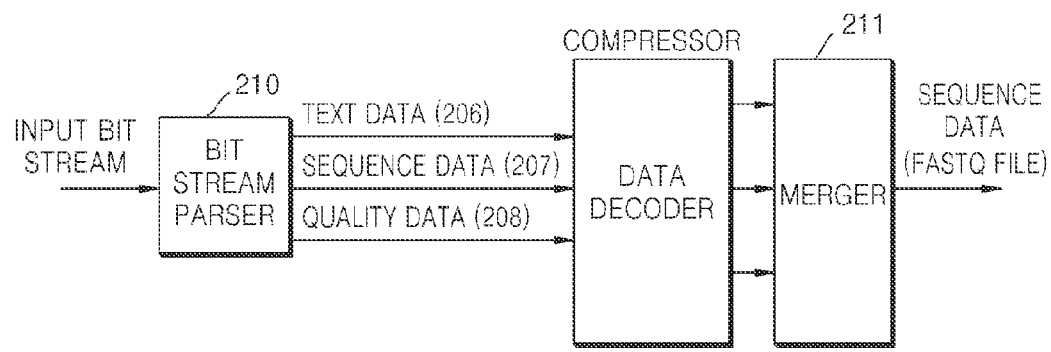
FIG. 2D illustrates a function of decompression, according to an embodiment of the present invention.

FIG. 2D illustrates the function of decompression, according to an embodiment of the present invention. Referring to FIG. 2D, the compressed bit stream is input. The bit stream parser 210 splits the bit stream, and the respective decoders for decoding text data 206, sequence data 207 and quality, data 208 then output the decompressed fields. Then, the fields are merged in the merger 209, and the original FASTQ file is output by the system. In the present embodiment, the encoding technique described here is lossless and preserves the order of the reads in the FASTQ file.

Figure 3:
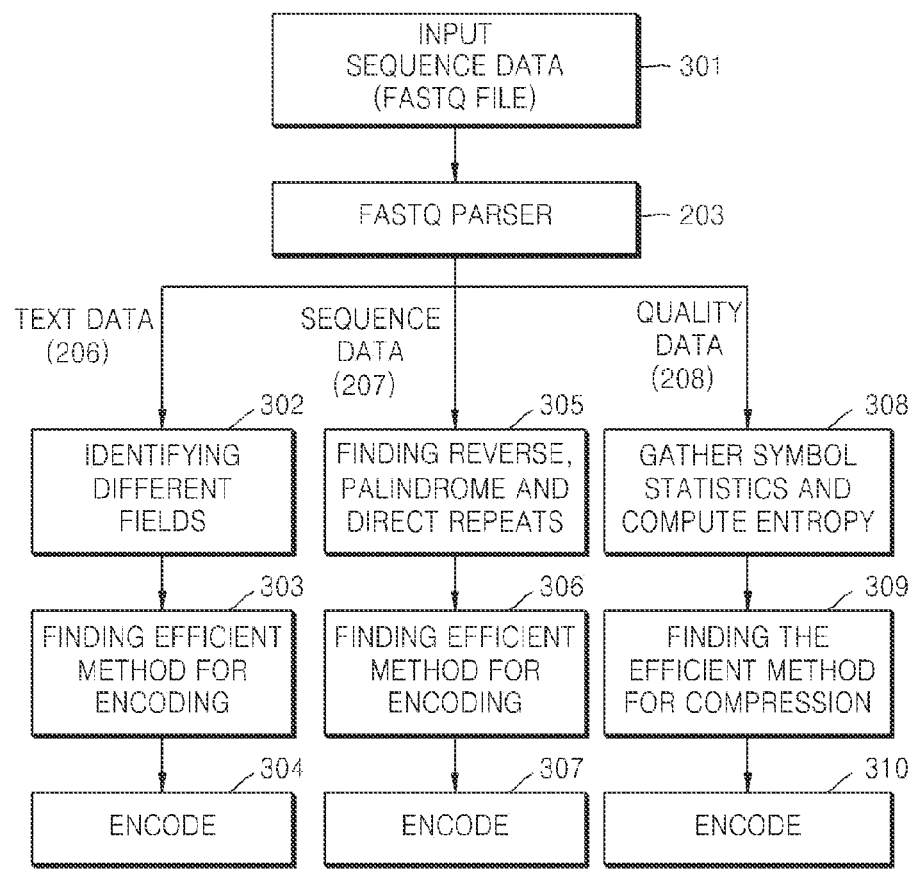
FIG. 3 illustrates encoding operations associated with different data fields of FASTQ file, according to an embodiment of the present invention.

FIG. 3 illustrates encoding operations associated with different data fields of FASTQ file, according to an embodiment of the present invention. Referring to FIG. 3, in operation 301, the input FASTQ file 301 is input. Then, the FASTQ parser 203 parses the file into text data 206, sequence data 207 and quality data 208. Text data comprises a title line (for instance, starting with @) and a third line (for instance, starting with +). The text fields vary over different FASTQ variants. Typically, the title lines in a given FASTQ file possess a large amount of redundancy with certain sub-strings repeating across almost all the title lines. In operation 302, the method identifies different fields in the title, considers title lines as a concatenation of repeating and variable fields, and stores the repeating fields only once as part of the header. In operation 303, the method identifies the efficient encoding method from among the plurality of methods for variable fields. Then, in operation 304, the method encodes the title by using the identified efficient method.

Furthermore, the DNA sequence data 207 that consists of symbols A, C, G and T corresponding to the four nucleotide bases is used. However, there may, be rare occurrences of symbol N (indicating an unknown base which can be any of A/C/G/T bases) and other symbols representing incompletely specified bases as per the IUB nomenclature. In operation 305, direct, palindromic and reverse repeats for blocks of sequence data are found and are carried out on each read by read basis. A palindromic sequence is a nucleic acid sequence (DNA or RNA) that is the same whether read 5' (five-prime) to 3° (three prime) on one strand or 5' to 3' on the complementary strand with which it forms a double helix. For example, the DNA sequence ACCTAGGT is palindromic because its nucleotide-by-nucleotide reversal is TGGATCCA, and reversing the order of the nucleotides in the complement gives the original sequence. The method identifies palindromic repeats in the DNA sequence. Furthermore, a dynamic dictionary is maintained with the read reads and is updated regularly in a first in, first out (FIFO) manner. The dynamic dictionary is used to find the repeats. The method updates this dynamic dictionary by using sequence read data by concatenating the reads to form a larger sequence or by considering them one by one with word size being equal to the read length. The dynamic dictionary may be used to find matches such as but not limited to exact and inexact repeats and reverse repeats.

Furthermore, in operation 306, the method finds the most efficient encoding method from among the plurality of methods by estimating entropies corresponding to encoding each of these repeats. The type of repeat is signaled followed by length of the repeat encoded, dictionary address and the mismatches if any. The skewed distribution of the mismatches is also employed to achieve efficient compression. In the present embodiment, if there is no repeat sequence found or the entropy calculated for these methods is higher than that of order-1 Markov encoding, the latter is used to encode the DNA sequence.

In operation 307, the method uses entropy coding such as but not limited to arithmetic coding to represent the type of encoding mechanism, used to compress each sub-part of read data. Also, the method uses arithmetic coding to efficiently represent the number of mismatches in blocks encoded as repeat.

The method then uses the quality data 208 in the input FASTQ file. Quality scores represent a probability of error in identifying a nucleotide base correctly that is outputted by the base calling methods. PHRED is a base-calling program for DNA sequence traces. PHRED reads DNA sequence chromatogram files and analyzes the peaks to call bases, assigning quality scores ("Phred scores") to each base call. PHRED quality scores are a de facto standard for representing the quality scores and are used in Sanger FASTQ, Illumina 1.3+ FASTQ and other NGS formats like SAM (Sequence Alignment Map) as well. Another variant of quality scores exists and is used in Solexa FASTQ format. These two variants of quality scores and the conversion therebetween are defined by using the following Equations:

$$Q_{PHRED} = -10 * \log_{10} P_e \qquad \text{(Equation 1)}$$

$$Q_{Solexa} = -10 * \log_{10}\left(\frac{P_e}{1 - P_e}\right) \qquad \text{(Equation 2)}$$

$$Q_{PHRED} = -10\log_{10}\left(10^{\left(\frac{Q_{Solexa}}{10}\right)} + 1\right) \qquad \text{(Equation 3)}$$

Quality Value (QV) scores are a per-base estimate of base caller accuracy. The range of these quality scores varies depending on the variant of the FASTQ file but is at most 94 (in the PHRED variant, the quality values are mapped from ASCII value 33-126, other variants map to a smaller range as compared to PHRED).

In operation 308, the method gathers symbol statistics. In operation 309, the method computes entropy for different representations of the quality scores, and obtains the efficient method/mechanism based on the symbol statistics which are then processed individually with the efficient encoding method to form the compressed bit-stream. In operation 310, the method encodes quality values by using the identified efficient method. The possible representations for the quality scores are described as below.

When it is assumed that the quality sequence is represented by x(n), the difference signal is represented as $$d(n)=x(n)-x(n-1) \qquad \text{(Equation 4)}$$

Also, x (−1) is assumed to be 33 (equivalently the symbol corresponding to ASCII 33). In the present embodiment, the quality values may be encoded by a suitable entropy coding mechanism such as but not limited to arithmetic coding, Huffman coding and the like.

Afterward, the method represents the quality scores as a concatenation of quality value (Qi) and corresponding run length (RLi). A run length is k−1 if the symbol is repeated k times in a string. These are then considered as separate symbols, and encoded by using adaptive arithmetic coding (AAC).

Then, the method takes <Qi, RLi> pair as symbols, resulting in a total of ($Q_{RANGE}$*Read Length$_{MAX}$) possible symbols. Furthermore, the method identifies the quality value which occurs a maximum number of times. In the present embodiment, the quality value is represented as Qmax. Then, the method represents the quality stream as a concatenation of three elements; offset, quality score and its run length. The offset is set to zero if the quality value is not the maximally occurring one and is set to the run length otherwise. Thus, the maximally occurring quality value is needed to be stored only once.

In another embodiment, the method identifies the quality value which occurs a maximum number of times. The quality stream is then represented in a novel manner as a concatenation of two elements; offset, and a composite symbol configured as tuple <quality score, its run length>. The offset is set to zero if the quality value is not the maximally occurring one and is set to the run length otherwise. Thus, it is necessary to store the maximally occurring quality value only once.

TABLE 1

| Input Quality stream IIIIIIIIIIIIIIIIIIIIIIIIIIIIIIII9IG9IC | |
|---|---|
| Method | Representation |
| 1 | IIIIIIIIIIIIIIIIIIIIIIIIIIIIIII9IG9IC |
| 2 | 40 0 0 0 0 0 0 0 0 0 0 0 0 0 0 0 0 0 0 0 0 −16 16 −2 −14 16 −6 |
| 3 | I 29 9 0 I 0 G 0 9 0 I 0 C 0 |
| 4 | I29 90 I0 G0 90 I0 C0 |
| 5 | 30 9 0 1 G 0 0 9 0 1 C 0 |
| 6 | 30 <9 0> 1 <G 0> 0 <9 0>1 <C 0> |

Table 1 above represents the quality stream in all the above described methods. The first difference is computed with a minimum quality score ($Q_{min}=33$). The proposed method first collects statistics for encoding the quality streams with the above described methods and then performs encoding by using the method with the greatest estimated compression gains.

Figure 4:
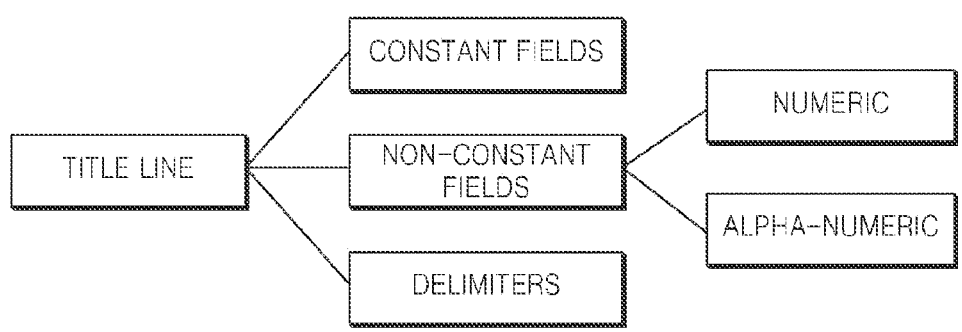
FIG. 4 is a block diagram illustrating different fields of title lines, according to an embodiment of the present invention.

FIG. 4 is a block diagram illustrating the different fields of the title lines, according to an embodiment of the present invention.

TABLE 2

Example title lines

SRR062635._1_ HWI-EAS110_103327062:4:1:<u>AX71</u>:_15970/1_ length = 100
SRR062635._2_ HWI-EAS110_103327062:4:1:<u>BY72</u>:_21126/1_ length = 100
SRR062635._3_ HWI-EAS110_103327062:4:1:<u>AT75</u>:_18579/1_ length = 100
SRR062635._964_ HWI-EAS110_103327062:4:1:<u>0C43</u>:_1046/2_ length = 100
SRR062635._1459_ HWI-EAS110_103327062:4:1:<u>9A62</u>:_910/2_ length = 100
SRR062635._1462_ HWI-EAS110_103327062:4:1:<u>CY22</u>:_979/2_ length = 100

| Equivalent representation | | |
|---|---|---|
| Constant fields | Length | Delimiter |
| SRR062635 | 9 | . |
| HWI-EAS110_103327062:4:1 | 24 | : |
| length = 100 | 10 | New line |
| Variable fields | Type | Delimiters |
| 1 Variable field | Alphanumeric | ; |
| 3 variable fields with mate pair information present in the third field | Numeric | ; & / |

NOTE:
Constant fields in bold, variable numeric in italic and alphanumeric in underline Table 2 above represents title lines as a concatenation of constant fields, variable fields and delimiters. The title lines in a given the possess a large amount of redundancy with certain sub-strings repeating in almost all the title lines. The proposed method considers title lines as a concatenation of repeating and non-repeating fields whereby the repeating fields as illustrated in Table 2 are stored only once in their compact representation as part of the header information. The non-repeating fields are further classified as numeric and alpha-numeric fields. The non-repeating alpha-numeric fields are encoded by using adaptive arithmetic coding using symbols 'A-Z' and '0-9'. For non-repeating numeric fields, the proposed method estimate the entropy, if coded directly, by using arithmetic coding treating the numbers as symbols or calculating the differential values and using these differential values as symbols for arithmetic coding. The method which results in a lower entropy value is used to code the numeric fields.

The header contains the nature of each field (repeating or non-repeating), and the type (numeric or alphanumeric). By default, all the constant fields are indicated as alphanumeric only. The proposed method also identifies the presence of mate pair information in the title lines. If found, then the information is efficiently encoded by using '1' and '2' as the only possible symbols. Many FASTQ files contain a field 'length' as represented in Table 2, followed by the length of a corresponding DNA sequence (which is the same as the length of quality data). If the field 'length' is present in the title lines, the proposed method discards the encoding of the field in which an appropriate flag to indicate the same is set. At the decoder end, this may be reconstructed by first decoding the sequence.

The proposed method is also capable of detecting any inconsistencies present in terms of the format of title lines. In this case, the above mentioned process continues until the point of consistency is reached, and the rest of the title line is encoded by using adaptive arithmetic coding, using the entire printable ASCII range as the symbol set. Then, the method checks whether the third line that starts with plus (−0 is a repeat of the title line. If not, a flag is sent to indicate the same. If the line comprises only the symbol '+', a flag to indicate the same is set, otherwise, a similar encoding methodology as used for the title lines is applied to these lines as well.

Figure 5:
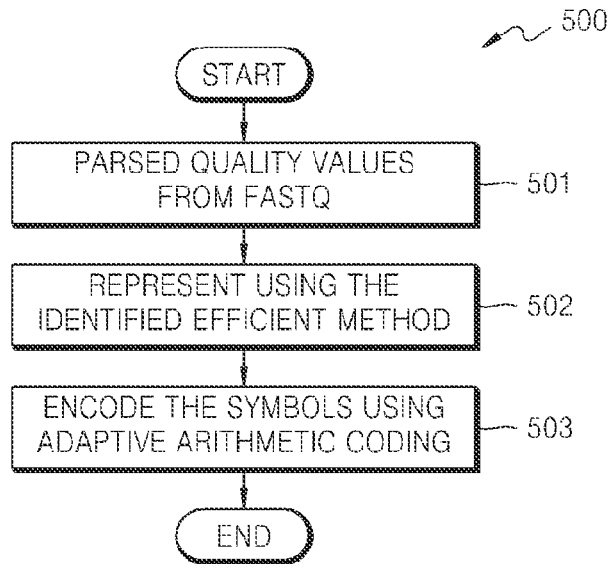
FIG. 5 illustrates a flowchart representing a method of encoding quality scores, according to an embodiment of the present invention.

FIG. 5 illustrates a flowchart representing the method of encoding quality scores, according to an embodiment of the present invention. Referring to a reference numeral 500 of FIG. 5, in operation 501, the method obtains the quality values parsed from FASTQ. Then, in operation 502, the method represents the parsed quality scores 501 by using the identified efficient method. Furthermore, in operation 503, the method encodes the symbols by using adaptive arithmetic coding.

In most of the FASTQ files, the ambiguous symbols (such as N) are accompanied by the lowest quality score $Q_{MIN}$. In this case, the proposed method shrinks the quality stream by removing all the quality values corresponding to ambiguous symbols in a sequence stream. In the present embodiment, the method identifies the occurrence of ambiguous symbols (e.g., detects ambiguous symbols) in input files and the associated quality scores. If the ambiguous symbols are always accompanied with the same quality score (lowest n most cases), then, the value thereof is encoded only once.

For files with multiple quality values corresponding to ambiguous symbols the proposed method uses an option of near-lossless compression, wherein the lowest quality score $Q_{MIN}$ is assigned to all ambiguous bases. However, for lossless compression, the same method is followed as described above without shrinking the quality stream.

Figure 6:
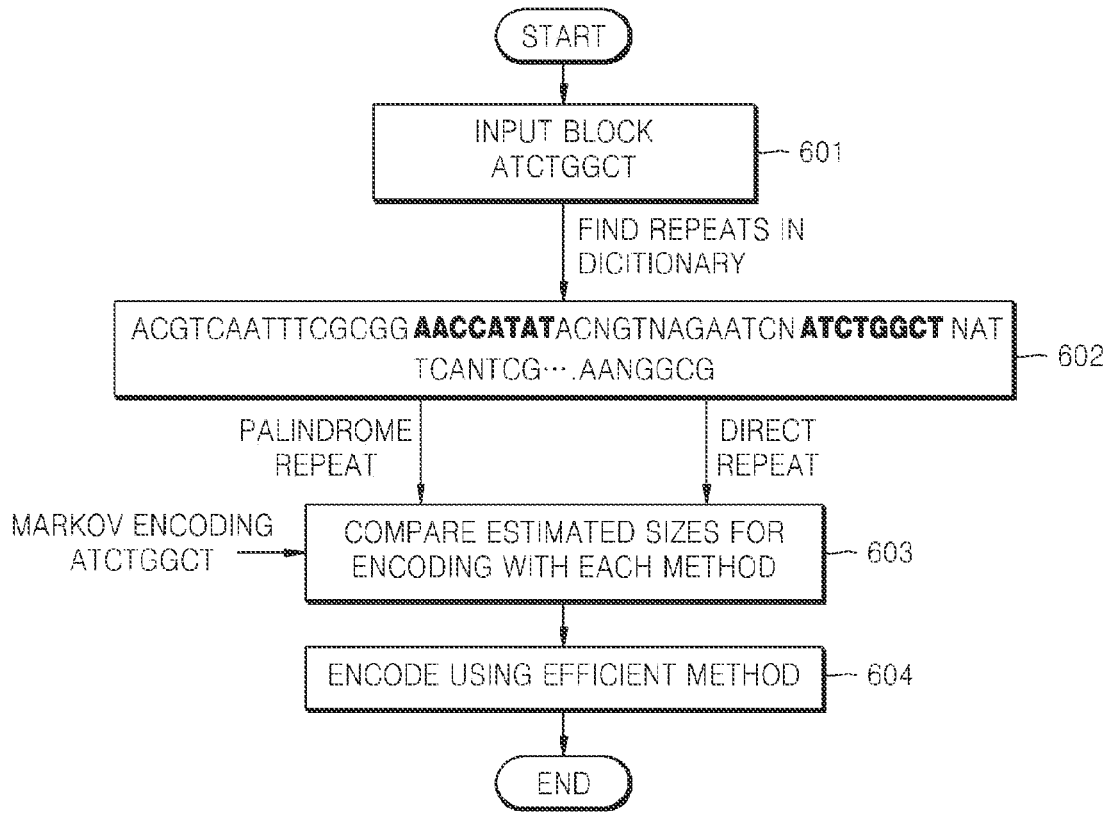
FIG. 6 illustrates an exemplary process of encoding a DNA sequence, according to an embodiment of the present invention, wherein the nucleotide sequence presented at 602 of FIG. 6 before the ellipsis is SEQ ID NO: 1.

FIG. 6 illustrates the exemplary process of encoding a DNA sequence, according to an embodiment of the present invention. Referring to FIG. 6, in operation 601, the input block with a DNA sequence is, for example, ATCTGGCT. In operation 602, the proposed method maintains a dynamic dictionary containing reads that are already processed and reads that are updated regularly in a FIFO manner. A hash table is used for indexing and fast repeat finding. The hash table is updated when reads are added to or removed from the dictionary. Whenever a new read is encoded, it is divided into blocks $B_1, B_2 \ldots B_n$. The block length is chosen to be constant for a given file and is determined based on the minimum read length determined in the initial pass. A large block length will reduce the probability of finding repeats while a smaller block length will result in an increased number of found repeats and the amount of overhead information. The method searches for approximate direct and palindromic repeats of the input block in the dictionary, and it allows a maximum of $NMM_{max}$ to be mismatched in a repeat. Both block length and $NMM_{max}$ may also be input by the user. If the given block is encoded as a repeat, the type of repeat is signaled by sending an appropriate flag followed by a length of the encoded repeat, a dictionary address, and the mismatches. If the repeat does not exactly match the number of mismatches $n_m$ ($\leq NMM_{max}$), a bitmask is employed so as to mark the positions of these mismatches. The bitmask is stored in a compressed form by using adaptive arithmetic coding with '0' and '1' as symbols. The size of the bit-stream corresponding to encoding of the given block such as a direct or a palindromic repeat is first estimated. In addition, the method also maintains the transition probabilities with respect to the nucleotide bases. These are used to estimate the bit-stream size if order-1 Markov encoding is employed to compress the block. The Markov encoding is used when no repeats for a block are found, if it gives better compression than encoding repeats, or when a remainder of one read is compressed after all blocks are compressed. In operation 603, the method compares estimated sizes for encoding with respect to each method. Then, in operation 604, it performs encoding by using the efficient method that is identified from the previous operations.

In the present embodiment, the dynamic dictionary is not stored in the compressed file, and is reconstructed at the decompressor end so as to decode the reads on a block by block basis. The read length is used to put these blocks together and to reconstruct the read.

Figure 7:
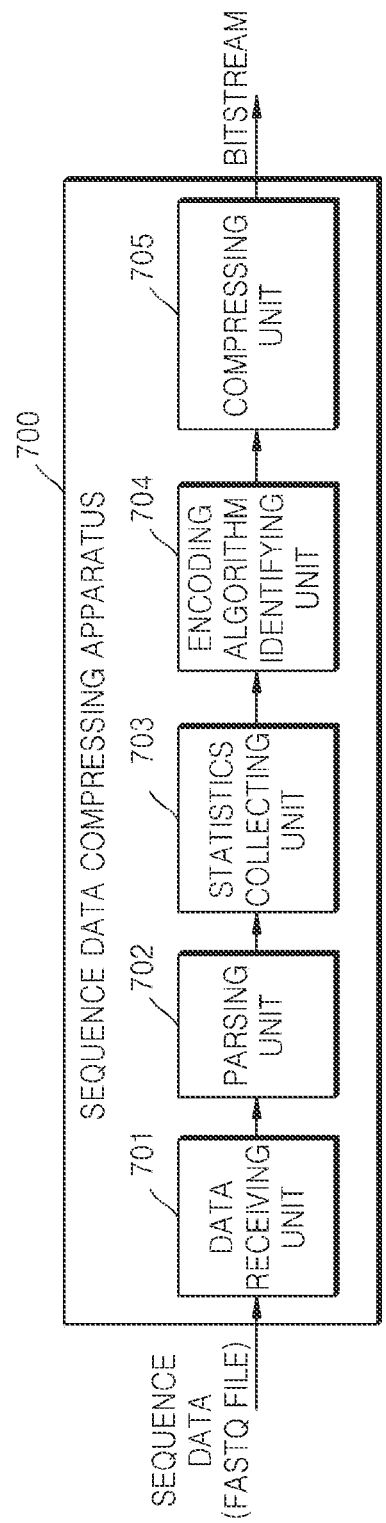
FIG. 7 illustrates a configuration of a sequence data compressing apparatus, according to an embodiment of the present invention.

FIG. 7 illustrates a configuration of a sequence data compressing apparatus 700, according to an embodiment of the present invention. Referring to FIG. 7, the sequence data compressing apparatus 700 includes a data receiving unit 701, a parsing unit 702, a statistics collecting unit 703, an encoding algorithm identifying unit 704, and a compressing unit 705. Furthermore, in order to prevent a characteristic of the present embodiment from being obscured, the sequence data compressing apparatus 700 of FIG. 7 only illustrates components that are related to the present embodiment. However, the sequence data compressing apparatus 700 of FIG. 7 may further include general components in addition to the components shown in FIG. 7.

The parsing unit 702, the statistics collecting unit 703, the encoding algorithm identifying unit 704, and the compressing unit 705 of the sequence data compressing apparatus 700 of FIG. 7 may be embodied as a general-use processor. That is, the processor may be embodied as an array of a plurality of logic gates or may be embodied as a microprocessor and combination of memories storing programs that are executable in the microprocessor. Alternatively, it will be obvious to those of ordinary skill in the art that the processor may be embodied as a different type of hardware.

Data to be processed by the sequence data compressing apparatus 700 of FIG. 7, and operations and functions of the sequence data compressing apparatus 700 are based on the aforementioned descriptions. Thus, it will be obvious to those of ordinary skill in the art that, although some descriptions that are described above are omitted here, the omitted descriptions may also be applied to the sequence data compressing apparatus 700.

The data receiving unit 701 receives sequence data in a text-based format, e.g., an FASTQ file format. The sequence data may correspond to data that is obtained by using NGS.

The parsing unit 702 parses a text of the sequence data into a plurality of fields, according to information included in the text. When the sequence data is in the FASTQ file format, the parsing unit 702 parses the text into the fields of one of a title line, a DNA sequence read, and a quality value.

The statistics collecting unit 703 collects statistics with respect to a symbol represented by strings that are included in each of the parsed fields. Here, the statistics collecting unit 703 collects the statistics with respect to sub-sections of each field of the parsed title line, the parsed DNA sequence read, and the parsed quality value.

The encoding algorithm identifying unit 704 identifies encoding algorithms that achieve the greatest compression gains with respect to the parsed fields, respectively, based on the collected statistics. That is, the encoding algorithm identifying unit 704 identifies an encoding algorithm for the title line, an encoding algorithm for the DNA sequence read, and an encoding algorithm for the quality value.

The compressing unit 705 encodes the sequence data by using each of the encoding algorithms for the parsed fields, and thus generates a bitstream that is a compression of the sequence data. Here, the compressing unit 705 may generated the unified bitstream by merging encoding results related to the title line, the DNA sequence read, and the quality value, by using an element such as the merger 209 of FIG. 2C.

Figure 8:
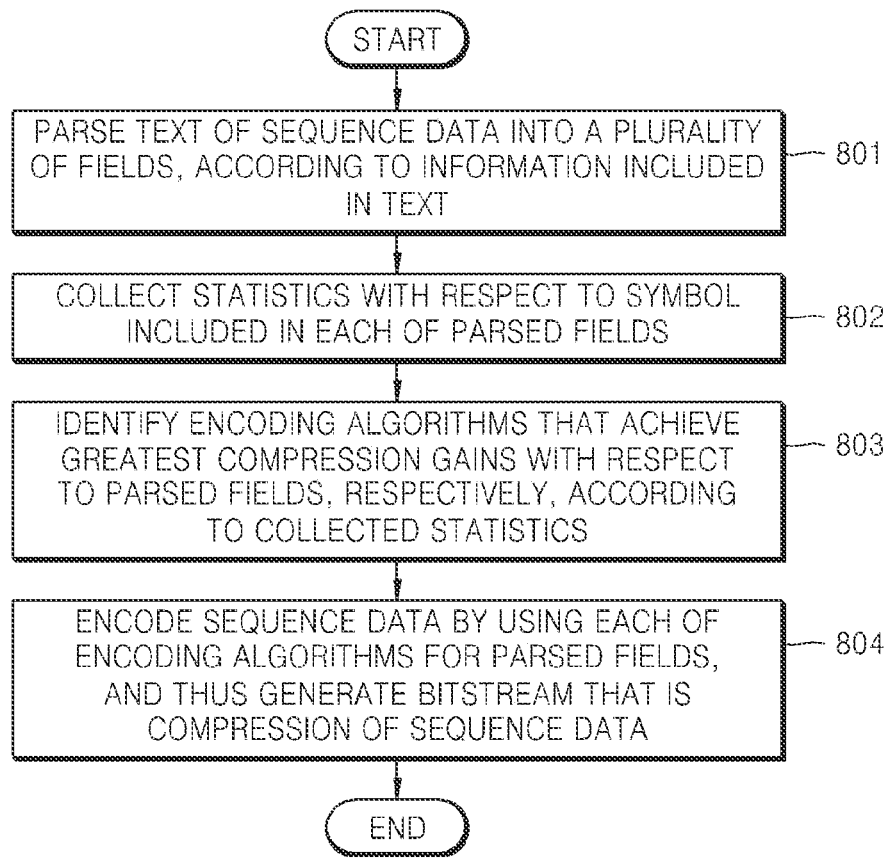
FIG. 8 is a flowchart of a method of compressing sequence data, according to an embodiment of the present invention.

FIG. 8 is a flowchart of a method of compressing sequence data, according to an embodiment of the present invention. Referring to FIG. 8, the method of compressing sequence data according to the present embodiment may include operations that are processed in chronological order by the sequence data compressing apparatus 700 of FIG. 7, and the descriptions described above with reference to FIGS. 1 through 6 may also be applied to the method. Thus, although some descriptions that are described above are omitted here, if the omitted descriptions are described above with reference to FIGS. 1 through 7, the omitted descriptions may also be applied to the method of compressing sequence data according to the present embodiment.

In operation 801, the parsing unit 702 parses a text of the sequence data into a plurality of fields, according to information included in the text.

In operation 802, the statistics collecting unit 703 collects statistics with respect to a symbol represented by strings that are included in each of the parsed fields.

In operation 803, the encoding algorithm identifying unit 704 identifies encoding algorithms that achieve the greatest compression gains with respect to the parsed fields, respectively, based on the collected statistics.

In operation 804, the compressing unit 705 encodes the sequence data by using each of the encoding algorithms for the parsed fields, and thus generates a bitstream that is a compression of the sequence data.

According to the one or more embodiments of the present invention, the sequence data in the text-based format which is obtained by using the NGS, e.g., the huge volumes of sequence data in the FASTQ format may be efficiently compressed with a higher compression gain, compared to the related art.

The embodiments of the present invention may be written as computer programs and may be implemented in general-use digital computers that execute the programs using a computer readable recording medium. In addition, a data structure used in the embodiments of the present invention may be written in a computer readable recording medium through various means. Examples of the computer readable recording medium include magnetic storage media (e.g., ROM, floppy disks, hard disks, etc), optical recording media (e.g., CD-ROMs, or DVDs), etc.

While this invention has been particularly shown and described with reference to exemplary embodiments thereof, it will be understood by those of ordinary skill in the art that various changes in form and details may be made therein without departing from the spirit and scope of the invention as defined by the appended claims. The exemplary embodiments should be considered in a descriptive sense only and not for purposes of limitation. Therefore, the scope of the invention is defined not by the detailed description of the invention but by the appended claims, and all differences within the scope will be construed as being included in the present invention.

What is claimed is:

1. A method of compressing genetic sequencing data in a text-based format, the method, implemented in a processor, comprising the steps of:
   receiving genetic sequencing data obtained using a high throughput genetic sequencing instrument;
   parsing information included in text of the genetic sequencing data into a plurality of fields, wherein the information comprises title information, sequence data and quality data and wherein the plurality of fields comprises a title information field, a sequence data field and a quality data field;
   collecting statistics with respect to a symbol represented by strings that are included in each of the plurality of fields;
   for each of the plurality of fields, identifying an encoding algorithm that achieves greatest compression gains with respect to the field based on the collected statistics, by determining, for each field of the genetic sequencing data, an optimized encoding algorithm selected from the group consisting of an arithmetic encoding algorithm, a Markov encoding algorithm, and a Huffman encoding algorithm;
   generating bitstreams, compressed from the genetic sequencing data, by encoding each of the plurality of fields of the genetic sequencing data using the respective identified encoding algorithm; and
   outputting a unified bitstream by merging the generated bitstreams encoded for each of the plurality of fields.

2. The method of claim 1, wherein the text of the genetic sequencing data includes a title line, and the method comprises parsing the title line information to identify constant fields, variable fields, and delimiters.

3. The method of claim 2, wherein the variable fields are further parsed to identify a numeric variable field and an alphanumeric variable field.

---

SEQUENCE LISTING

```
<160> NUMBER OF SEQ ID NOS: 1

<210> SEQ ID NO 1
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 1
acgtcaattt cgcggaacca tatacngtna gaatcnatct ggctnattca ntcg            54
```

4. The method of claim 3, wherein the optimized encoding algorithm for a field is algorithms are identified by employing computing an entropy calculations for the numeric variable field.

5. The method of claim 1, wherein the text-based format is an FASTQ format.

6. The method of claim 1 further comprising, before the parsing the text, determining an origin of the genetic sequencing data in the text-based format, said origin comprising a sequencing system type selected from the group consisting of SoLiD, illumine, 454 and Helicos.

7. The method of claim 1, wherein, if the genetic sequencing data includes a length field representing a length of a DNA sequence read comprised in the text, the method comprises discarding a value of the field length before collecting the statistics.

8. The method of claim 1, wherein collecting the statistics comprises checking for inconsistencies between title lines included in the text.

9. The method of claim 1, wherein collecting the statistics comprises identifying a quality value (Qmax) with a maximum occurrence in the text.

10. The method of claim 9, wherein a quality stream for each read included in the text is represented as an offset, a quality symbol, and a run length.

11. The method of claim 9, wherein the quality value in a quality stream is represented as offset and <quality symbol, run length>.

12. The method of claim 1, further comprising detecting ambiguous symbols in quality scores included in the text, wherein generating the bitstreams comprises encoding the occurrence once.

13. The method of claim 12, further comprising allocating a lowest quality value to each position corresponding to an ambiguous symbol in the text, and
wherein the generating the bitstreams includes using a result of the allocation.

14. The method of claim 1, wherein the bitstreams are generated using lossless compression or near-lossless compression.

15. The method of claim 1, wherein the parsing text of the genetic sequencing data comprises parsing a DNA sequence read included in the text by identifying repeats and non-repeats.

16. A non-transitory computer-readable medium having recorded thereon a program for executing a method of claim 1.

17. An apparatus for compressing genetic sequencing data in a text-based format, the apparatus including a processor and a non-transitory processor-readable medium having processor-executable instructions stored thereon, the processor-executable instructions comprising instructions for:
receiving genetic sequencing data obtained using a high throughput genetic sequencing instrument;
parsing information included in text of the genetic sequencing data into a plurality of fields, wherein the information includes title information, sequence data and quality data and wherein the plurality of fields includes a title information field, a sequence data field and a quality data field;
collecting statistics with respect to one or more symbols represented by strings that are included in each of the plurality of fields;
identifying, for each of the plurality of fields, an encoding algorithm that achieves greatest compression gains with respect to the field based on the collected statistics, by determining, for each field of the genetic sequencing data, an optimized encoding algorithm selected from the group consisting of an arithmetic encoding algorithm, a Markov encoding algorithm, and a Huffman encoding algorithm;
generating bitstreams, compressed from the genetic sequencing data, by encoding each of the plurality of fields of the genetic sequencing data using the respective identified encoding algorithm; and
outputting a unified bitstream by merging the generated bitstreams encoded for each of the plurality of fields.

18. The apparatus of claim 17, wherein the instructions for parsing include instructions for parsing the title information line included in the text so as to identify constant fields, variable fields, and delimiters.

19. The apparatus of claim 18, wherein the instructions for parsing include instructions for parsing the variable fields to identify a numeric variable field and an alphanumeric variable field.

20. The apparatus of claim 19, wherein the instructions for coding include instructions for identifying the optimized encoding algorithm for a field algorithms by employing computing an entropy calculation for the numeric variable field.

21. The apparatus of claim 17, wherein the instructions for collecting statistics includes instructions for collecting the statistics by identifying a quality value (Qmax) with a maximum occurrence in the text.

22. The apparatus of claim 21, wherein a quality stream for each read included in the text is represented as an offset, a quality symbol, and a run length, and
wherein the quality value in the quality stream is represented as offset and <quality symbol, run length>.

23. The apparatus of claim 17, wherein the instructions for collecting statistics includes instructions for determining an occurrence of ambiguous symbols in quality scores included in the text, and
wherein the instructions for generating include generating the bitstreams by encoding the occurrence once.

24. The apparatus of claim 23, wherein the instructions for collecting statistics includes instructions for allocating a lowest quality value to all positions corresponding to ambiguous bases in the text, and
wherein the instructions for generating include instructions for generating the bitstreams by using a result of the allocating.

25. The apparatus of claim 17, wherein the instructions for generating include instructions for generating the bitstreams using lossless compression or near-lossless compression.

26. The apparatus of claim 17, wherein the instructions for parsing include instructions for parsing a DNA sequence read included in the text by identifying repeats and non-repeats.

* * * * *